US006056135A

United States Patent [19]

Widman

[11] Patent Number: 6,056,135

[45] Date of Patent: May 2, 2000

[54] LIQUID TRANSFER DEVICE TO FACILITATE REMOVAL OF LIQUID FROM A CONTAINER BY A SYRINGE

[76] Inventor: Michael L. Widman, 156 Vista Del Diablo, Danville, Calif. 94526

[21] Appl. No.: 08/991,515

[22] Filed: Dec. 16, 1997

[51] Int. Cl.[7] .......... B65D 39/00; A61B 19/00

[52] U.S. Cl. .......... 215/50; 215/47; 215/247; 215/355; 215/DIG. 3; 604/415

[58] Field of Search .......... 215/247, 249, 215/277, 355, DIG. 3, 50, 48, 47; 604/415, 403, 905

[56] References Cited

U.S. PATENT DOCUMENTS

| | | | |
|---|---|---|---|
| 2,601,091 | 6/1952 | Butler et al. | 215/DIG. 3 X |
| 2,797,837 | 7/1957 | Roberts | 604/415 X |
| 3,330,282 | 7/1967 | Visser et al. | 215/355 X |
| 4,163,500 | 8/1979 | Gunne et al. | 215/355 X |
| 4,303,071 | 12/1981 | Smith . | |
| 4,317,448 | 3/1982 | Smith . | |
| 5,085,332 | 2/1992 | Gettig et al. | 215/249 |
| 5,240,047 | 8/1993 | Hedges . | |
| 5,348,550 | 9/1994 | Ikeda et al. | 215/DIG. 3 X |
| 5,356,406 | 10/1994 | Schraga . | |
| 5,383,906 | 1/1995 | Burchett et al. . | |
| 5,467,878 | 11/1995 | Derksen . | |
| 5,573,525 | 11/1996 | Watson et al. . | |
| 5,833,089 | 11/1998 | Manni et al. | 215/DIG. 3 X |
| 5,874,048 | 2/1999 | Seto et al. | 215/355 X |

FOREIGN PATENT DOCUMENTS

| | | | |
|---|---|---|---|
| 1321493 | 2/1963 | France | 215/247 |

*Primary Examiner*—Nathan J. Newhouse
*Attorney, Agent, or Firm*—Thomas R. Lampe

[57] ABSTRACT

A liquid transfer device for use in combination with a container and a syringe to facilitate removal of liquid from a container by the syringe includes an obstruction member positioned in an outlet of the container. The obstruction member has a concave inner surface facing the container interior to direct liquid to a passageway in the obstruction member when the container is inverted. A seal is formed between the obstruction member and the syringe spout and the spout is positioned by the obstruction member with the distal end of the spout located either in the passageway or projecting from the passageway toward the container interior and disposed closely adjacent to the inner surface of the obstruction member.

9 Claims, 2 Drawing Sheets

LIQUID TRANSFER DEVICE TO FACILITATE REMOVAL OF LIQUID FROM A CONTAINER BY A SYRINGE

TECHNICAL FIELD

This invention relates to a liquid transfer device for use in combination with a container and with a syringe to facilitate removal of liquid from the container by the syringe. The syringe is of the type incorporating a tubular-shaped spout known and used, for example, to dispense medicines and other liquids to the mouths of babies or into baby bottles or other receptacles.

BACKGROUND OF THE INVENTION

Syringes incorporating tubular-shaped spouts are known and such prior art devices are employed, for example, to extract the liquid contents of a container and dispense the extracted liquid to the mouths of infants or into baby bottles or other receptacles.

U.S. Pat. No. 5,383,906, issued Jan. 24, 1995, for example, discloses an integrated nursing bottle and liquid medication dispensing apparatus which utilizes a syringe mounted coaxially within the baby bottle to dilute the contents of the bottle with fluid from the syringe. Such patent, however, does not address problems encountered when extracting the liquid contents of a container through use of a syringe.

U.S. Pat. No. 5,573,525, issued Nov. 12, 1996, discloses a bottle with a closure element for receiving a syringe having a spout and cooperable with the syringe to extract the bottle contents. When transferring the liquid, the bottle remains upright and liquid flows through a tube having an inlet at or near the bottle bottom. Of course, with such an arrangement extraction of all or substantially all the liquid is not assured. For example, the tube inlet may be displaced from the bottom and spaced from the liquid at the bottom, especially if the bottle is tilted. Furthermore, the tube adds to the complexity and cost of the device. Also, air may enter the syringe from the tube, at least during the initial stage of extraction.

Syringes incorporating spouts do not cooperate with existing prior art containers in such a way as to ensure removal of virtually all the contents of the container when such contents are transferred through the spout into the syringe barrel interior by retracting the plunger of the syringe. That is, utilizing prior art approaches, extracting the liquid contents of the container with a syringe can and often does leave a significant portion of the liquid in the container.

This problem is solved through use of the invention disclosed and claimed herein wherein an obstruction member such as a plug is located at the container outlet. The obstruction member cooperates with the spout of a syringe positioned in an opening formed in the obstruction member to form a fluid-tight seal therebetween and to simultaneously position the spout relative to the obstruction member with the distal end of the spout located either in the passageway or projecting from the passageway toward the container interior and disposed closely adjacent to the inner surface of the obstruction member.

Devices are disclosed in existing patents which cooperate with a syringe having an injection needle to position the needle relative to a bottle of medicine or the like for purposes of locating the needle relative to the container. Such arrangements are disclosed, for example, in U.S. Pat. No. 5,240,047, issued Aug. 31, 1993, U.S. Pat. No. 5,356,406, issued Oct. 18, 1994, and U.S. Pat. No. 5,467,878, issued Nov. 21, 1995.

These latter prior art arrangements are not suitable for use with a syringe having a spout rather than a needle. Furthermore, such prior art arrangements do not cooperate with a syringe in such a manner as to promote extraction of virtually all of the contents of a container by the syringe.

DISCLOSURE OF INVENTION

The present invention relates to a liquid transfer device for use in combination with a container and with a syringe to facilitate removal of liquid from the container by the syringe. The device is characterized by its relative simplicity, low cost, and ease of use when extracting the contents of a container.

The container is of the type having a container body defining a container interior and having a container outlet attached to the container body defining an outlet opening in communication with the container interior.

The syringe is of the type including a barrel defining a barrel interior and a spout extending from the barrel and defining a passageway in communication with the barrel interior. The spout has a distal end and an external tapered spout surface tapering in the direction of the distal end.

The liquid transfer device comprises an obstruction member positionable at the container outlet of the container to obstruct the outlet opening defined by the container outlet. The obstruction member has an inner surface facing the container interior when the obstruction member obstructs the outlet opening.

The obstruction member additionally has an interior wall defining a passageway leading from the inner surface to a location external of the container. The interior wall is engageable with the spout of the syringe to form a fluid-tight seal therewith and to simultaneously position the spout relative to the obstruction member with the distal end of the spout located either in the passageway or projecting from the passageway toward the container interior and disposed closely adjacent to the inner surface of the obstruction member.

The inner surface of the obstruction member is concave and contiguous with the interior wall for directing fluid to the passageway when the container is inverted to position the container body over the container outlet.

Other features, advantages, and objects of the present invention will become apparent with reference to the following description and accompanying drawings.

BEST MODE FOR CARRYING OUT THE INVENTION

Figure 1:
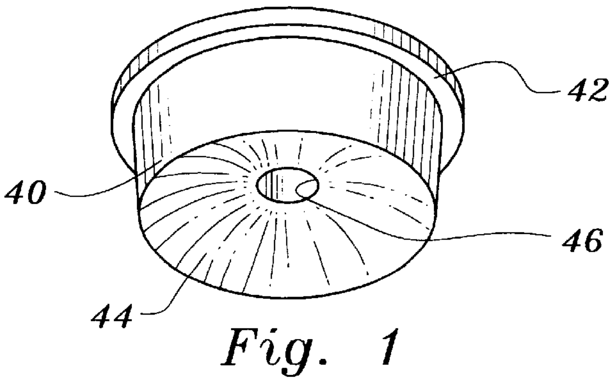
FIG. 1 is a perspective view of the obstruction member of the invention.
Figure 2:
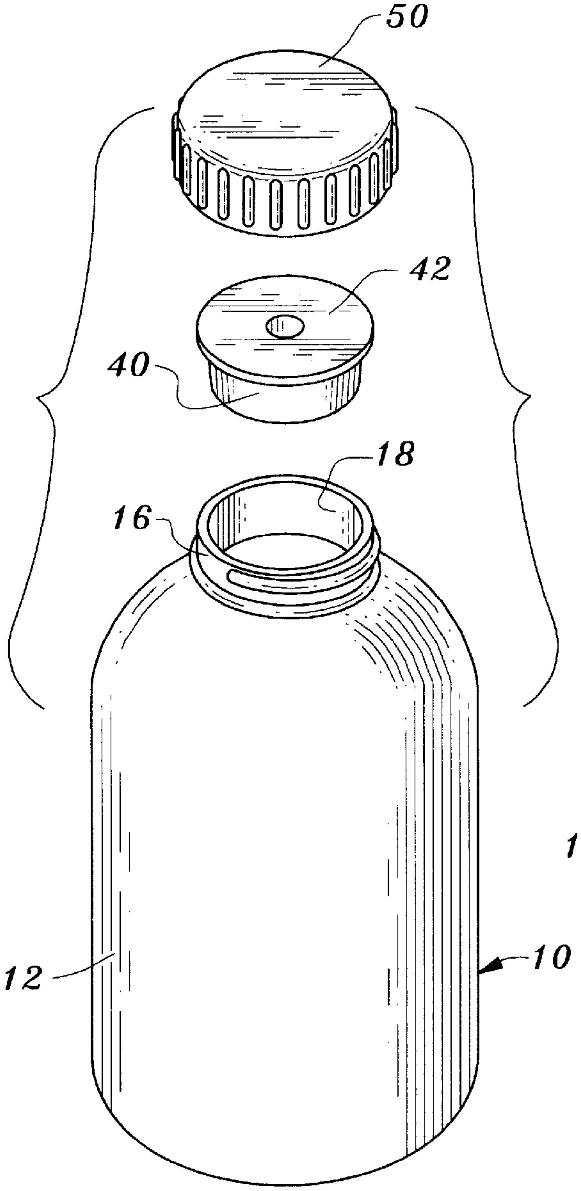
FIG. 2 is an exploded perspective view illustrating a container, the obstruction member and a closure member.
Figure 3:
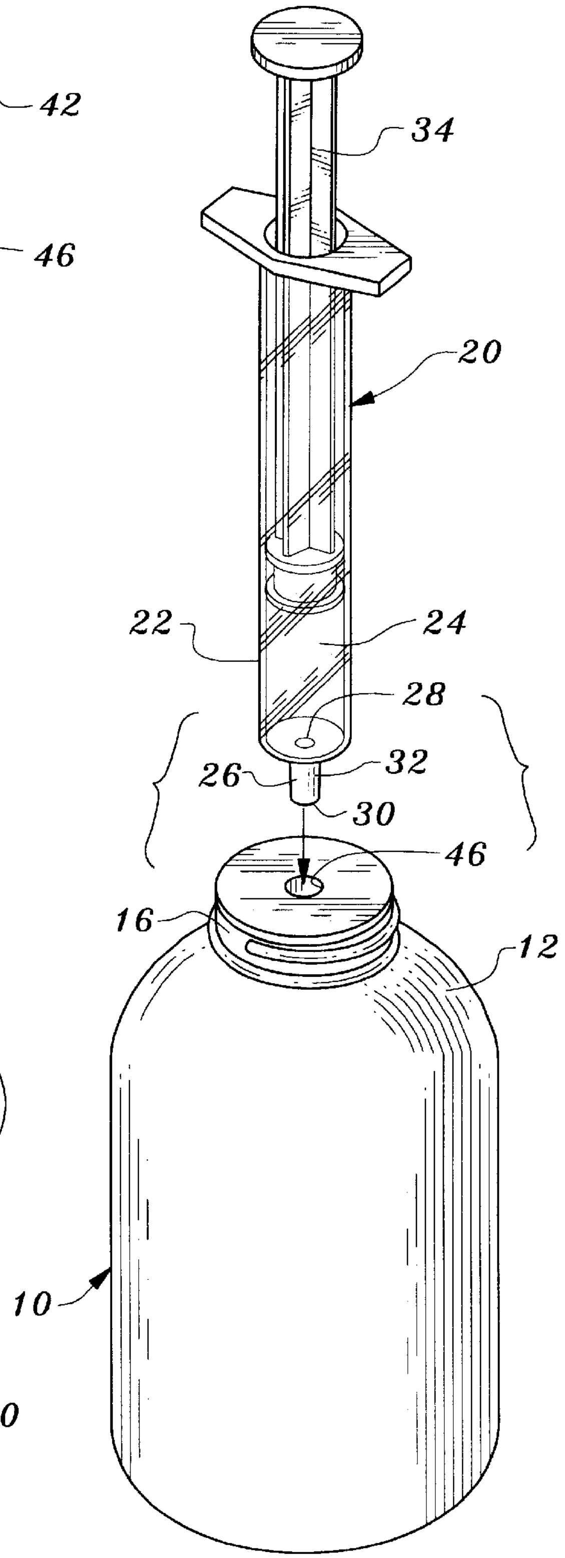
FIG. 3 is a perspective view illustrating a syringe prior to engagement thereof with the obstruction member mounted on the container.

Referring now to the drawings, a conventional container 10 for liquid medicines or other liquids is illustrated. The container includes a container body 12 defining a container interior 14 and a threaded container outlet 16 integrally attached to the container body and defining an outlet opening 18 in communication with the container interior.

Also shown in the drawings is a syringe 20 including a barrel 22 defining a barrel interior 24 and a spout 26 extending from the barrel and defining a passageway 28 in communication with the barrel interior. The spout has a distal end 30 and an external tapered spout surface tapering in the direction of the distal end. A plunger 34 is slidably disposed within the barrel interior to either cause liquid to flow into the barrel interior through the spout passageway or cause liquid in the barrel interior to be dispensed outwardly through the spout passageway.

The structure thus far described and relating to the container and syringe is well known in the prior art.

The objective of the liquid transfer device of the present invention is to facilitate removal of liquid from the container by the syringe. More particularly, it is an objective of the present invention to enable the syringe to extract virtually the entire liquid contents of the container and transfer same to the barrel interior through the spout.

Referring now to FIGS. 1–5, a preferred form of the invention is illustrated and comprises an obstruction member 40 formed of rubber, plastic or other suitable resilient material. The obstruction member 40 has a plug-like configuration and is sized and configured so as to enter outlet opening 18 of the container and form a fluid-tight seal with the container outlet so that the obstruction member obstructs the outlet opening.

A flange 42 is connected to and radiates outwardly from the obstruction member. When the obstruction member is positioned in place on the container, the flange 42 will engage the top of the container outlet or neck to limit inward movement of the obstruction member relative to the container.

The obstruction member 40 has an inner surface 44 which faces the container interior when the obstruction member obstructs the outlet opening. Inner surface 44 is concave.

The obstruction member 40 has an interior wall defining a passageway 46 leading from the inner surface 44 to a location external of the container.

Figure 5:
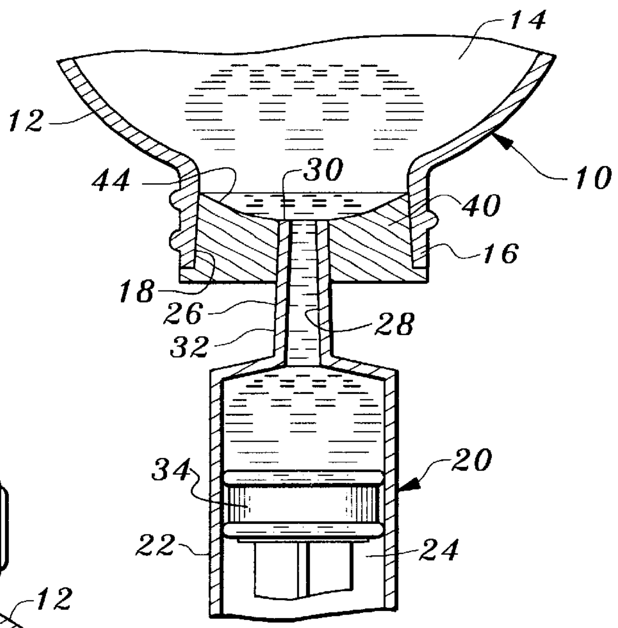
FIG. 5 is an enlarged, cross-sectional view illustrating a portion of the container in inverted condition and the syringe in position to extract the liquid contents thereof.
Figure 4:
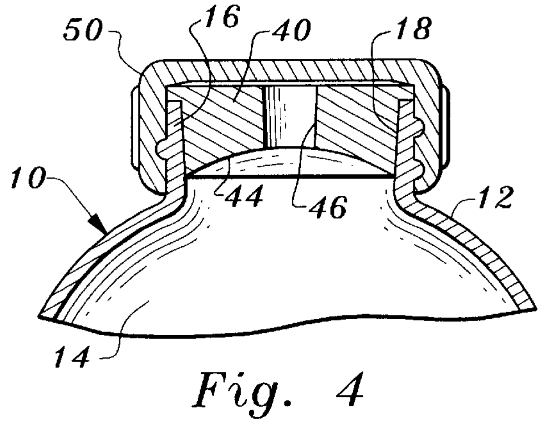
FIG. 4 is an enlarged, cross-sectional view illustrating a top portion of the container and the obstruction member and closure member applied thereto.

The concave inner surface 44 is contiguous with the interior wall defining passageway 46 and directs fluid to the passageway when the container is inverted to position the container body over the container outlet. Such a position is shown in FIG. 5. The passageway 44 has a circular cross-section and the inner surface is coaxial with the passageway.

The interior wall defining passageway 46 is tapered and the passageway progressively diminishes in size in the direction of the inner surface 44. The taper of the interior wall corresponds to the taper of the tapered spout surface 32 of spout 26.

A screw type closure member 50 (FIGS. 2 and 4) is releasably connectable to the container outlet by threads (not shown) on the closure member corresponding to those at the container outlet. Closure member 50 covers the obstruction member when connected to the container outlet.

One wishing to transfer the contents of the container 12 to the syringe first removes closure member 50. The spout 26 of the syringe is then inserted into passageway 46 in the manner shown in FIG. 3. The interior wall defining the passageway 46 forms a fluid-tight seal with the syringe spout when engaged thereby. Furthermore, the passageway and spout are sized and configured so as to simultaneously position the spout relative to the obstruction member with the distal end of the spout located either in the passageway or projecting from the passageway toward the container interior and disposed closely adjacent to the inner surface of the obstruction member. In FIG. 5 the distal end 30 of the spout is located in the passageway 46 precisely at the location where passageway 46 intersects inner surface 44. FIG. 5 also shows the liquid contents of the container being transferred into the syringe barrel interior (due to retraction of the plunger 34). It will be appreciated that virtually all of the liquid contents of the container can be extracted by the syringe, the concave inner surface 44 directing the liquid in the container under the influence of gravity to passageway 46 and spout 26 disposed therein.

Figure 7:
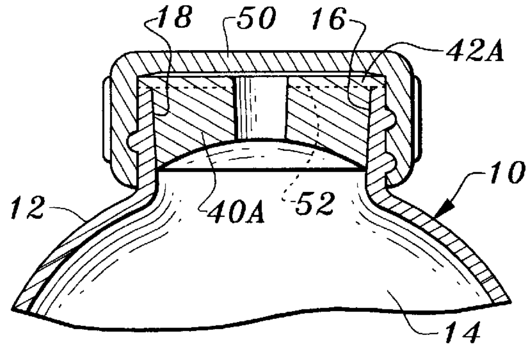
FIG. 7 is a view similar to FIG. 4 but illustrating the alternative embodiment.
Figure 6:
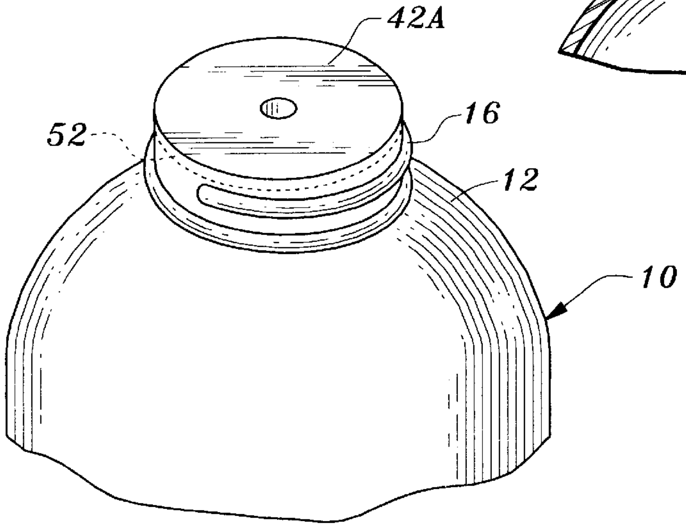
FIG. 6 is a perspective view of an alternative embodiment of the invention connected to the top portion of a container.

FIGS. 6–7 disclose an alternative embodiment of the invention wherein obstruction member 40A is integrally attached to container outlet 16 by a frangible interconnection between flange 42A and the container outlet or neck. One wishing to remove the obstruction member from the container can manually break the frangible interconnection along line of weakness 52 formed between the container outlet or neck and the flange 42A.

What is claimed is:

1. A liquid transfer device for use in combination with a container and with a syringe to facilitate removal of liquid from the container by the syringe, the container having a container body defining a container interior and having a container outlet attached to said container body defining an outlet opening in communication with the container interior and the syringe including a barrel defining a barrel interior and a spout extending from the barrel and defining a passageway in communication with the barrel interior, said spout having a distal end and an external tapered spout surface tapering in the direction of said distal end, said liquid transfer device comprising an obstruction member positionable at the container outlet of the container to obstruct the outlet opening defined by the container outlet, said obstruction member having an inner surface facing the container interior when said obstruction member obstructs the outlet opening, and said obstruction member additionally having an interior wall defining a passageway leading from said inner surface to a location external of said container, said interior wall engageable with the spout of the syringe to form a fluid-tight seal therewith and to simultaneously position the spout relative to the obstruction member with the distal end of the spout located either in said passageway or projecting from the passageway toward the container interior and disposed closely adjacent to the inner surface of said obstruction member, said liquid transfer device being integrally attached to said container outlet by attachment means and said attachment means providing a frangible interconnection between said liquid transfer device and said container outlet.

2. The liquid transfer device according to claim 1 wherein said obstruction member is formed of resilient material and has an outer surface for frictional engagement with said container outlet to maintain said liquid transfer device connected to said container.

3. The liquid transfer device according to claim 1 additionally comprising a closure member releasably connectable to said container outlet, said closure member covering said obstruction member when connected to said container outlet.

4. The liquid transfer device according to claim 1 wherein the inner surface of said obstruction member is concave and contiguous with said interior wall for directing fluid to said passageway when said container is inverted to position said container body over said container outlet.

5. The liquid transfer device according to claim 4 wherein said passageway has a circular cross-section, said inner surface being coaxial with said passageway.

6. The liquid transfer device according to claim 1 wherein said interior wall is tapered and wherein said passageway progressively diminishes in size in the direction of said inner surface.

7. The liquid transfer device according to claim 6 wherein the taper of said interior wall corresponds to the taper of the external tapered spout surface of the spout.

8. The liquid transfer device according to claim 1 additionally comprising container outlet engagement means attached to said obstruction member for engaging said container outlet to limit movement of said obstruction member relative to said container outlet.

9. The liquid transfer device according to claim 8 wherein said container outlet engagement means comprises a flange radiating outwardly from said obstruction member.

* * * * *